US011013525B2

(12) United States Patent
Takei

(10) Patent No.: US 11,013,525 B2
(45) Date of Patent: May 25, 2021

(54) TREATMENT TOOL

(71) Applicant: Olympus Corporation, Hachioji (JP)

(72) Inventor: Yusuke Takei, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 188 days.

(21) Appl. No.: 16/261,653

(22) Filed: Jan. 30, 2019

(65) Prior Publication Data

US 2019/0150969 A1    May 23, 2019

Related U.S. Application Data

(63) Continuation of application No. PCT/JP2016/072808, filed on Aug. 3, 2016.

(51) Int. Cl.
*A61B 17/29* (2006.01)
*A61B 90/00* (2016.01)

(52) U.S. Cl.
CPC ........ *A61B 17/29* (2013.01); *A61B 2017/293* (2013.01); *A61B 2017/2925* (2013.01);
(Continued)

(58) Field of Classification Search
CPC ....... A61B 17/29; A61B 17/28; A61B 17/282; A61B 17/2909; A61B 17/2926;
(Continued)

(56) References Cited

U.S. PATENT DOCUMENTS 5,383,888 A    1/1995  Zvenyatsky et al.
5,792,135 A  * 8/1998  Madhani .......... A61B 17/00234
606/1
(Continued)

FOREIGN PATENT DOCUMENTS

JP    2009-261609    11/2009
JP    2009-539567    11/2009
(Continued)

OTHER PUBLICATIONS

International Search Report and Written Opinion from corresponding International Application No. PCT/JP2016/072808, dated Nov. 8, 2016.
(Continued)

*Primary Examiner* — Vi X Nguyen
(74) *Attorney, Agent, or Firm* — Oliff PLC

(57) ABSTRACT

A treatment tool includes a housing and a rotary element configured to be attached to the housing so as to define the treatment tool for treating an examinee. The rotary element is defined by an elongated member being rotatable about a rotational axis with respect to the housing. A rotary member is attached to the elongated member to rotate the elongated member. The rotary member is disposed coaxially with the elongated member and rotatable with respect to the housing. A locking member is used for unlocking the elongated member from the housing for rotation in response to rotation of the rotary member to allow the elongated member to rotate in the same direction as the rotary member in response to rotation of the rotary member and locking the elongated member against rotation with respect to the housing upon stopping of relative rotation between the rotary member and the housing.

8 Claims, 10 Drawing Sheets

(52) U.S. Cl.
CPC ............... *A61B 2017/2927* (2013.01); *A61B 2017/2929* (2013.01); *A61B 2017/2933* (2013.01); *A61B 2017/2946* (2013.01); *A61B 2090/035* (2016.02)

(58) Field of Classification Search
CPC ...... A61B 17/22031; A61B 17/320092; A61B 2017/2927; A61B 2017/2925; A61B 2017/2946; A61B 2017/2933; A61B 2017/292
See application file for complete search history.

(56) References Cited

U.S. PATENT DOCUMENTS

| | | | |
|---|---|---|---|
| 7,214,230 B2 * | 5/2007 | Brock | ............... A61B 17/0469 606/139 |
| 2007/0287993 A1 | 12/2007 | Hinman et al. | |
| 2010/0057121 A1 | 3/2010 | Piskun et al. | |
| 2014/0277107 A1 | 9/2014 | Ishida et al. | |
| 2016/0345995 A1 | 12/2016 | Takei | |

FOREIGN PATENT DOCUMENTS

| | | |
|---|---|---|
| JP | 2014-176483 | 9/2014 |
| JP | 2015-154931 | 8/2015 |
| WO | 2007146894 | 12/2007 |
| WO | 2015122353 | 8/2015 |

OTHER PUBLICATIONS

Dec. 30, 2020 Office Action issued in Chinese Patent Application No. 201680088252.1.

* cited by examiner

TREATMENT TOOL

CROSS-REFERENCE TO RELATED APPLICATION

This application is a continuation application of PCT Application No. PCT/JP2016/072808 filed on Aug. 3, 2016, which is hereby incorporated by reference in its entirety.

TECHNICAL FIELD

The disclosed technology relates to a treatment tool for treating a treatment target with an end effector.

DESCRIPTION OF THE RELATED ART

U.S. Pat. No. 5,383,888 discloses a treatment tool including an end effector, disposed on the distal-end portion of a shaft thereof, for treating a treatment target. The treatment tool has a housing that can be held by hand, and the shaft is coupled to the housing. When a handle on the housing is opened away from or closed on a grip of the housing, a pair of gripping members of the end effector are opened or closed. When the gripping members are closed, they grip the treatment target, such as a living tissue or the like, therebetween. A rotary member, or rotary knob, that is integral with the shaft is mounted on the housing for rotation about the central axis of the shaft. When an operating force for rotating the rotary member is applied, the shaft and the end effector rotate in unison with the rotary member with respect to the housing about the central axis of the shaft that serves as a predetermined rotational axis. The angular position of the end effector about the predetermined rotational axis is now varied. In addition, in this treatment tool, the end effector is bendable with respect to the shaft, or the central axis of the shaft, based on a manipulation of a bend manipulator, or wing member, on the housing.

The treatment tool disclosed in U.S. Pat. No. 5,383,888 may perform a treatment process while the end effector is being bent with respect to the shaft. In such a treatment process, a force may act on the end effector at a position spaced from the central axis of the shaft. In this case, the force acting on the end effector tends to produce an angular moment about the central axis of the shaft, causing the shaft to rotate in unison with the end effector.

BRIEF SUMMARY OF EMBODIMENTS

It is an object of the disclosed technology to provide a treatment tool that effectively prevents an end effector and a shaft from rotating due to a force acting on the end effector.

One aspect of the disclosed technology is directed to a treatment tool comprises a housing and a rotary element configured to be attached to the housing so as to define the treatment tool for treating an examinee. The rotary element is defined by an elongated member being rotatable about a rotational axis with respect to the housing. A rotary member is attached to the elongated member to rotate the elongated member. An end effector is attached to the elongated member. The rotary member is disposed coaxially with the elongated member and rotatable with respect to the housing. A locking member is used for unlocking the elongated member from the housing for rotation depending on relative rotation between the rotary member and the housing in response to rotation of the rotary member to allow the elongated member to rotate in the same direction as the rotary member in response to rotation of the rotary member and locking the elongated member against rotation with respect to the housing upon stopping of relative rotation between the rotary member and the housing. The elongated member is prevented from being rotated about the rotational axis with respect to the locking member. The rotary member includes a cam surface defining a range in which the locking member is movable depending on rotation of the rotary member with respect to the housing. The locking member has a biasing member exerting biasing forces tending to cause the locking member to be fitted in the housing and an abutting portion abutted by the cam surface of the rotary member. The cam surface has a central portion disposed centrally in the range. The biasing member exerts the biasing forces thereof upon stopping of relative rotation between the rotary member and the housing to place the abutting portion of the locking member on the central portion.

Another aspect of the disclosed technology is directed to a treatment tool comprises a housing and a rotary element configured to be attached to the housing so as to define the treatment tool for treating an examinee. The rotary element is defined by an elongated member being rotatable about a rotational axis with respect to the housing. A rotary member is attached to the elongated member to rotate the elongated member. An end effector is attached to the elongated member. The rotary member is disposed coaxially with the elongated member and rotatable with respect to the housing. A locking member is used for unlocking the elongated member from the housing for rotation depending on relative rotation between the rotary member and the housing in response to rotation of the rotary member, to allow the elongated member to rotate in the same direction as the rotary member in response to rotation of the rotary member, and locking the elongated member against rotation with respect to the housing upon stopping of relative rotation between the rotary member and the housing. The rotary member includes a cam surface defining a range in which the locking member is movable depending on rotation of the rotary member with respect to the housing. The locking member has an abutting portion abutted by the cam surface of the rotary member. The cam surface and the abutting portion together define a movement until the rotary member is rotated with respect to the housing so as to rotate the locking member and the elongated member with respect to the housing.

A further aspect of the disclosed technology is directed to a treatment tool comprises a housing and an elongated member having a proximal-end side and a distal-end side. The proximal-end side is attached to the housing. The distal-end side attaching to an end effector treating an examinee. The elongated member is rotatable about a rotational axis with respect to the housing. A rotary member is disposed coaxially with the elongated member. The rotary member is rotatable with respect to the housing. The rotary member is configured to rotate the shaft. The rotary member having a cam surface and the cam surface having a central portion. A locking member is configured to lock the elongated member with respect to the housing. The locking member is configured to unlock the elongated member from the housing by being added a rotational power beyond a limit to the rotary member. The locking member includes a biasing member and an abutting portion. The biasing member is configured to exert biasing forces so as to cause the locking member to be fitted in the housing. The abutting portion is abutted by the cam surface of the rotary member. The biasing member is configured to exert the biasing forces to place the abutting portion on the central portion of the cam surface when the rotary member is not rotated. The housing has an immovable fitting portion and the locking member has a movable fitting portion movable in response to rotation of the rotary member. The movable fitting portion fitting to the immovable fitting portion so that the elongated member is not rotatable with respect to the housing. The movable fitting portion not fitting to the immovable fitting portion so that the elongated member is rotatable with respect to the housing. The cam surface and the abutting portion together define a movement until the rotary member is rotated with respect to the housing to rotate the locking member and the shaft with respect to the housing.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

Embodiments of the present disclosure will hereinafter be described with reference to the drawings.

Figure 1:
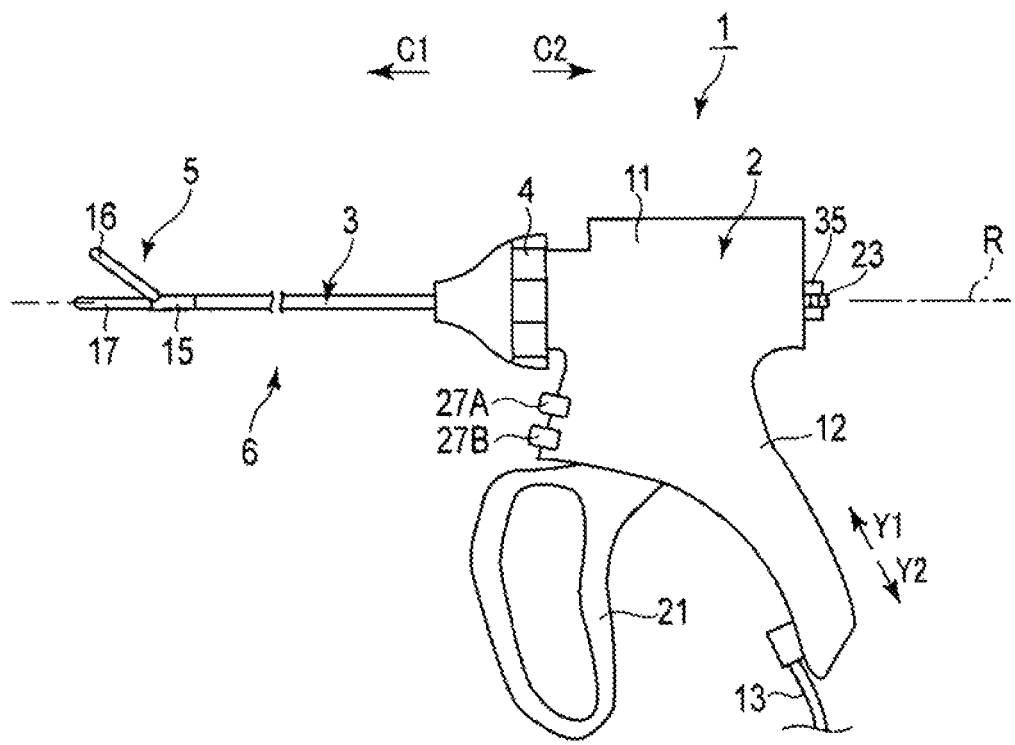
FIG. 1 is a schematic view illustrating a treatment tool according to a first embodiment of the present disclosure.

A first embodiment will be described below with reference to FIGS. 1 through 4B. FIG. 1 is a view illustrating a treatment tool 1, or gripping treatment tool, according to the present embodiment. The treatment tool 1 illustrated in FIG. 1 has a predetermined rotational axis R, or longitudinal axis. One side in a direction along the predetermined rotational axis R will be referred to as a distal-end side, or arrow C1 side, whereas the side opposite the distal-end side as a proximal-end side, or arrow C2 side.

The treatment tool 1 includes a housing 2, an elongated member as a shaft 3, or sheath, projecting from the housing 2, a rotary knob 4, or rotary member, disposed outside of the housing 2 and the shaft 3, and an end effector 5 disposed on the distal-end portion of the shaft 3. The rotary knob 4 is disposed coaxially with the shaft 3. The end effector 5 is used to treat an examinee. The shaft 3, the rotary knob 4, and the end effector 5 jointly make up a rotary element 6 about the predetermined rotational axis R on the housing 2. In other words, the rotary element 6 has the shaft 3, the rotary knob 4, and the end effector 5.

The shaft 3 extends along the predetermined rotational axis R from the proximal-end side toward the distal-end side. The shaft 3 is rotatably supported on the housing 2 for rotation about the predetermined rotational axis R. Therefore, the shaft 3 supports the end effector 5 such that the end effector 5 is rotatable in unison with the shaft 3 about the predetermined rotational axis R. A side of the shaft 3 that lies toward the housing 2 is referred to as a proximal-end side, and another side of the shaft 3 that lies toward the end effector 5 as a distal-end side. The end effector 5 may be disposed on the predetermined rotational axis R or may be disposed off the predetermined rotational axis R. According to the present embodiment, as described hereinafter, the end effector 5 is movable between a position on the predetermined rotational axis R on the shaft 3 and a position off the predetermined rotational axis R. According to the present disclosure, therefore, the end effector 5 is bendable with respect to the shaft 3.

The shaft 3 is made of a metal material such as stainless steel, for example. The shaft 3 should preferably be elastically deformable under the load of an external force F (see FIG. 2) applied to the rotary element 6 from a direction off the predetermined rotational axis R. Consequently, the shaft 3 should preferably be flexible appropriately under the load of an external force F applied to the rotary element 6 from a direction off the predetermined rotational axis R.

The housing 2 is made of a resin material that is electrically insulative. According to the present embodiment, the housing 2 includes a housing body 11 extending along the predetermined rotational axis R and a grip 12, or fixed handle, extending from the housing body 11 in directions transverse to the predetermined rotational axis R, or directions indicated by the arrows Y1 and Y2. The grip 12 is disposed in a region spaced from the predetermined rotational axis R. One end of a cable 13 is connected to the grip 12. The other end of the cable 13 is connected to an energy control device (not illustrated). Here, directions that are transverse, or substantially perpendicular, to the predetermined rotational axis R and that are transverse, or substantially perpendicular, to the directions in which the grip 12 extend are referred to as widthwise directions of the housing 2, or directions substantially perpendicular to the sheet of FIG. 1. FIG. 1 is a view in which the treatment tool 1 is viewed from one of the widthwise directions of the housing 2.

Figure 2:
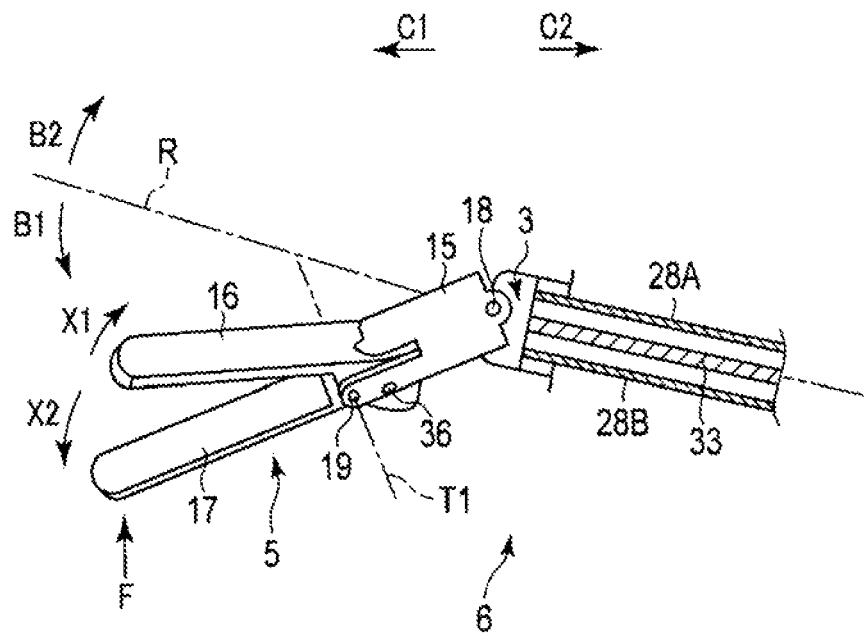
FIG. 2 is a schematic perspective view illustrating a configuration of an end effector of the treatment tool according to the first embodiment.

FIG. 2 is a view illustrating the configuration of the end effector 5. As illustrated in FIGS. 1 and 2, the end effector 5 is rotatable in unison with the shaft 3 about the rotational axis R with respect to the housing 2. The end effector 5 is also bendable or curvable with respect to the shaft 3. When the shaft 3 is rotated about the rotational axis R, the angular position of the end effector 5 about the rotational axis R varies. Directions in which the end effector 5 is bendable, or the directions indicated by the arrows B1 and B2, are transverse, or substantially perpendicular, to the predetermined rotational axis R. The end effector 5 includes a junction member 15, a first gripping member 16, and a second gripping member 17. The junction member 15 is mounted on the distal end of the shaft 3 for bending movement with respect to the shaft 3. In other words, a bendable joint 18 is disposed between the shaft 3 and the junction member 15. On the end effector 5, the space between the gripping members 16 and 17 can be opened and closed. The gripping members 16 and 17 can be opened and closed in directions, or in the directions indicated by the arrows X1 and X2, that are transverse to the rotational axis R and to the directions in which the end effector 5 is bendable.

As illustrated in FIG. 2, the first gripping member 16 is angularly movably mounted on the junction member 15 by a support pin 19, or support portion. That is, the support pin 19 that supports the first gripping member 16 is mounted on the junction member 15. The first gripping member 16 is angularly movable about the support pin 19. According to the present embodiment, the first gripping member 16 is angularly movable with respect to the junction member 15 about a pivot axis T1 that extends through the support pin 19 and is substantially coaxial with the support pin 19. The pivot axis T1 extends substantially parallel to the directions in which the end effector 5 is bendable. In other words, the directions in which the pivot axis T1 extends are transverse to the rotational axis R on the shaft 3 and to the directions in which the gripping members 16 and 17 are opened and closed. When the first gripping member 16 is angularly moved about the support pin 19, or support portion, the first gripping member 16 is opened or closed with respect to the second gripping member 17. The support pin 19, or support portion, is rotatable in unison with the shaft 3 and the end effector 5 about the predetermined rotational axis R with respect to the housing 2.

According to an embodiment, the second gripping member 17 is integral with or fixed to the junction member 15. According to another embodiment, the second gripping member 17 is also angularly movably mounted on the junction member 15. According to still another embodiment, a rod member (not illustrated) extends from within the junction member 15 toward the distal-end side, and a portion of the rod member that projects from the junction member 15 toward the distal-end side functions as the second gripping member 17.

As illustrated in FIG. 1, a handle 21, or movable handle, is angularly movably mounted on the housing 2. When the handle 21, which is an opening and closing manipulation entering portion, is angularly moved with respect to the housing 2, the handle 21 is opened or closed with respect to the grip 12. In other words, the handle 21 is openable and closable with respect to the grip 12. According to the present embodiment, the treatment tool 1 is pistol-shaped such that the handle 21 is positioned on the side of the rotational axis R where the grip 12 is positioned and is positioned more closely to the distal-end side than the grip 12. When the handle 21 is opened and closed with respect to the grip 12, the handle 21 moves in directions substantially parallel to the rotational axis R. According to an embodiment, the handle 21 may be positioned more closely to the proximal-end side than the grip 12. According to another embodiment, the handle 21 and the grip 12 may be disposed opposite each other across the rotational axis R, and when the handle 21 is opened and closed with respect to the grip 12, the handle 21 may move in directions substantially perpendicular to the rotational axis R.

According to the present embodiment, a bend dial 23 is mounted as a bend manipulation entering portion, or manipulation entering portion, on the housing 2. When the bend dial 23 is angularly moved, for example, a manipulation is entered to bend the end effector 5 with respect to the shaft 3. As illustrated in FIG. 2, the shaft 3 houses therein bend actuating members 28A and 28B such as wires, leaf springs, or the like extending along the rotational axis R. The bend actuating members 28A and 28B have distal ends, or one ends, connected to the junction member 15 of the end effector 5. The bend actuating members 28A and 28B have proximal ends mechanically coupled to the bend dial 23 over a pulley (not illustrated) disposed in the housing 2. When the bend dial 23, or the bend manipulation entering portion, enters a manipulation, a manipulating force is transmitted to the bend actuating members 28A and 28B, which are moved along the predetermined rotational axis R with respect to the shaft 3 and the housing 2. The end effector 5 is now bent in one of bent directions, or the directions indicated by the arrows B1 and B2, with respect to the shaft 3.

The rotary knob 4 is supported on the distal-end side of the housing body 11. The rotary knob 4 should preferably be made of a resin material that is electrically insulative. In order to produce a large angular moment with a small force, the rotary knob 4 has a maximum radius, or a distance from the rotational axis R, D0 that is large to an appropriate extent compared with a maximum radius, or a distance from the rotational axis R, D1 of the shaft 3.

The bend actuating members 28A and 28B are rotatable in unison with the shaft 3, the rotary knob 4, and the end effector 5 about the predetermined rotational axis R with respect to the housing 2. The bend dial 23 may be rotatable in unison with the shaft 3 and the end effector 5 about the predetermined rotational axis R with respect to the housing 2. The bend dial 23 may not be rotatable in unison with the shaft 3, the rotary knob 4, and the end effector 5 about the predetermined rotational axis R. According to the present embodiment, the bend dial 23 is mounted on a proximal-end face of the housing body 11. However, the position of the bend dial 23 is not limited to the proximal-end face of the housing body 11. A bend manipulation entering portion such as the bend dial 23 may be mounted on an outer surface of the housing body 11 which faces away from the side of the predetermined rotational axis R where the grip 12 is positioned, for example.

Manipulating buttons 27A and 27B are mounted on the housing 2. When each of the manipulating buttons 27A and 27B is pressed, it enters a manipulation. When each of the manipulating buttons 27A and 27B enters a manipulation, the treatment tool 1 is operated in a predetermined operation mode. At this time, as with known treatment tools, any of a high-frequency current, ultrasonic vibrations, and heater-generated head is applied as a treatment energy to a treatment target gripped by the gripping members 16 and 17. According to an embodiment, when the treatment tool 1 is operated in a predetermined operation mode based on a manipulation entered by either one of the manipulating buttons 27A and 27B, an electric motor may be energized to drive a staple to piece the treatment target gripped by the gripping members 16 and 17.

Figure 3:
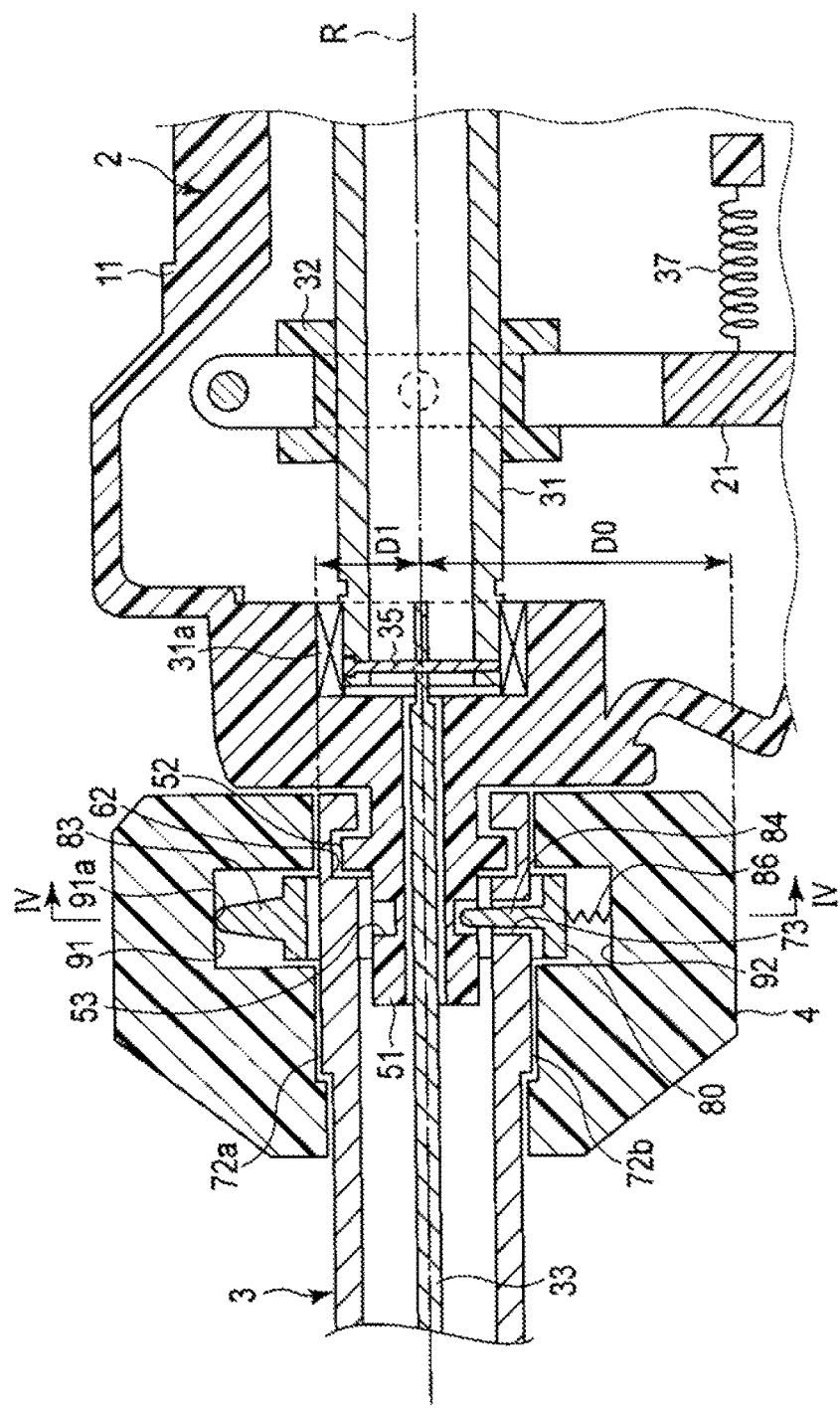
FIG. 3 is a schematic cross-sectional view illustrating an inner configuration of a rotary knob and a shaft on a housing of the treatment tool according to the first embodiment.

FIG. 3 is a view illustrating an inner configuration of the housing 2. FIG. 3 illustrates a cross section substantially perpendicular, or transverse, to the widthwise directions of the housing 2. In FIG. 3, the bend actuating members 28A and 28B, a configuration for transmitting manipulating forces from the bend dial 23 to the bend actuating members 28A and 28B, and so on are omitted from illustration. As illustrated in FIG. 3, a tubular movable member 31 extends along the predetermined rotational axis R in the housing 2, or the housing body 11. The movable member 31 is supported by a support member 31a such as a hollow cylindrical roller bearing or the like, for example, for rotation about the predetermined rotational axis R. However, the movable member 31 is prevented from rotating about the rotational axis R with respect to the shaft 3. The movable member 31 is rotatable in unison with the shaft 3 and the end effector 5 about the predetermined rotational axis R with respect to the housing 2.

When the handle 21 is opened with respect to the grip 12, the first gripping member 16 is relatively opened with respect to the second gripping member 17. When the handle 21 is closed with respect to the grip 12, the first gripping member 16 is relatively closed with respect to the second gripping member 17. Various mechanisms may be employed for thus opening and closing the first gripping member 16 with respect to the second gripping member 17.

A slider 32 is disposed on an outer circumferential surface of the movable member 31 in the housing 2 according to the present embodiment. The handle 21 is coupled to the movable member 31 by the slider 32. The movable member 31 is rotatable about the predetermined rotational axis R with respect to the handle 21. A drive rod 33 as an opening and closing drive member is fixed to the movable member 31 by a connection pin 35 in the housing 2. The drive rod 33 extends from within the movable member 31 through the shaft 3 along the rotational axis R. Since the drive rod 33 is fixed to the movable member 31, when a manipulating force is applied from the rotary knob 4 to the drive rod 33, the drive rod 33 is rotated in unison with the shaft 3, the end effector 5, and the movable member 31 about the predetermined rotational axis R with respect to the housing 2.

A handle biasing member 37 such as a spring or the like is disposed in the housing 2. The handle biasing member 37 has an end connected to the housing 2 and another end connected to the handle 21. The handle biasing member 37 normally biases the handle 21 so as to be opened with respect to the grip 12.

When a manipulating force is applied to the handle 21 to open or close the handle 21 with respect to the grip 12, the movable member 31 and the drive rod 33 are moved along the predetermined rotational axis R with respect to the shaft 3 and the housing 2. As illustrated in FIG. 2, the drive rod 33, or drive member, that extends in the shaft 3 has an end, or distal end, connected to the first gripping member 16 of the end effector 5. According to the present embodiment, the drive rod 33 is connected to the first gripping member 16 by a coupling pin 36. When the movable member 31 and the drive rod 33, or drive member, are moved along the predetermined rotational axis R, at least the first gripping member 16 is angularly moved about the support pin 19 with respect to the junction member 15. The space between the gripping members 16 and 17 is now opened or closed. At this time, the support pin 19 functions as a pivot point about which the first gripping member 16 is angularly moved, and the coupling pin 36 functions as a point where a drive force from the drive rod 33 acts on the first gripping member 16. According to the embodiment in which the second gripping member 17 is also angularly movable with respect to the junction member 15, the distal end of the drive rod 33, or opening and closing drive member, is also connected to the second gripping member 17 as well as the first gripping member 16. In this case, when the drive rod 33 is moved along the rotational axis R, both the gripping members 16 and 17 are angularly moved with respect to the junction member 15, opening or closing the space between the gripping members 16 and 17.

According to the present embodiment, the handle biasing member 37 normally biases the first gripping member 16 so as to be opened with respect to the second gripping member 17, so that the end effector 5 is normally biased to open the space between the gripping members 16 and 17.

Figure 4A:
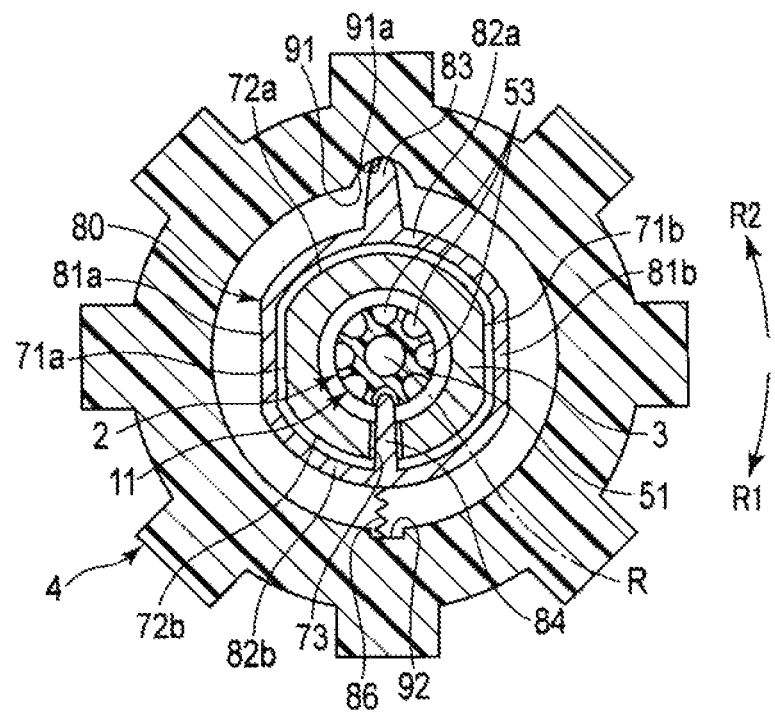
FIG. 4A is a schematic cross-sectional view taken along line IV-IV of FIG. 3, illustrating the manner in which the rotary knob of the treatment tool according to the first embodiment is not rotated.
Figure 4B:
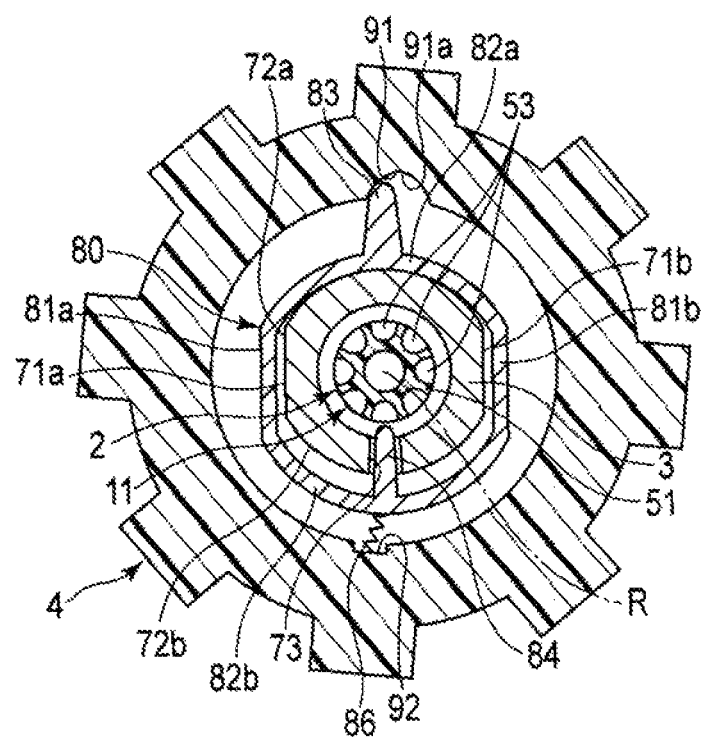
FIG. 4B is a schematic cross-sectional view taken along line IV-IV of FIG. 3, illustrating the manner in which the rotary knob of the treatment tool according to the first embodiment is rotated about a predetermined rotational axis.

As illustrated in FIGS. 3 through 4B, the housing body 11 of the housing 2 includes a hollow cylindrical tubular portion 51 on a distal-end portion thereof. The tubular portion 51 has on an outer circumferential surface thereof a fitting portion 52, or fitting protrusion, that is fitted in an inner circumferential surface of the shaft 3. The shaft 3 has a fitting portion 62, or fitting recess, defined in the inner circumferential surface of a proximal-end portion thereof and fitted over the fitting portion 52 of the housing 2. The fitting portion 62 in the inner circumferential surface of the proximal-end portion of the shaft 3 is of an annular shape. The fitting portion 52 on the distal-end portion of the housing 2 that is fitted in the fitting portion 62 in the proximal-end portion of the shaft 3 allows the shaft 3 to rotate about the predetermined rotational axis R while preventing the shaft 3 from moving along the predetermined rotational axis R with respect to the housing 2.

The tubular portion 51 on the distal-end portion of the housing 2 has a plurality of grooves 53, which may be through holes, defined in an outer circumferential surface thereof. The grooves 53, or fixed fitting portions, extend radially away from the predetermined rotational axis R. An inner protrusion 84 of a locking member 80 to be described hereinafter is fitted in one of the grooves 53.

The shaft 3 has a pair of flat faces 71a and 71b and a pair of arcuate faces 72a and 72b on an outer circumferential surface of a proximal-end portion thereof. The flat faces 71a and 71b should preferably lie parallel to each other such that lines normal thereto are oriented away from each other. The arcuate faces 72a and 72b should preferably be part of arcs around the predetermined rotational axis R. One of the arcuate faces 72a and 72b of the shaft 3 has a through hole 73 extending between inner and outer sides of the shaft 3. The through hole 73 extends radially away from the predetermined rotational axis R.

The locking member 80 is fitted over the outer circumferential surface of the proximal-end portion of the shaft 3. The locking member 80 has a pair of straight rods 81a and 81b and a pair of arcuate rods 82a and 82b. The straight rods 81a and 81b should preferably lie parallel to each other. The arcuate rods 82a and 82b should preferably be part of arcs around the predetermined rotational axis R of the shaft 3. The locking member 80 further includes an outer protrusion 83, or abutting portion, and an inner protrusion 84, or movable fitting portion. The outer protrusion 83 is disposed on one of the arcuate rods 82a and 82b, or the arcuate rod 82a in the illustrated embodiment. The outer protrusion 83 protrudes radially outwardly away from the predetermined rotational axis R. The inner protrusion 84 is disposed on the other of the arcuate rods 82a and 82b, or the arcuate rod 82b in the illustrated embodiment. The inner protrusion 84 protrudes toward the predetermined rotational axis R, or radially inwardly. The inner protrusion 84 of the locking member 80 is continuously fitted in the through hole 73. The inner protrusion 84 of the locking member 80 can also be fitted in one of the grooves 53 defined in the tubular portion 51 on the distal-end portion of the housing 2.

Figure 5:
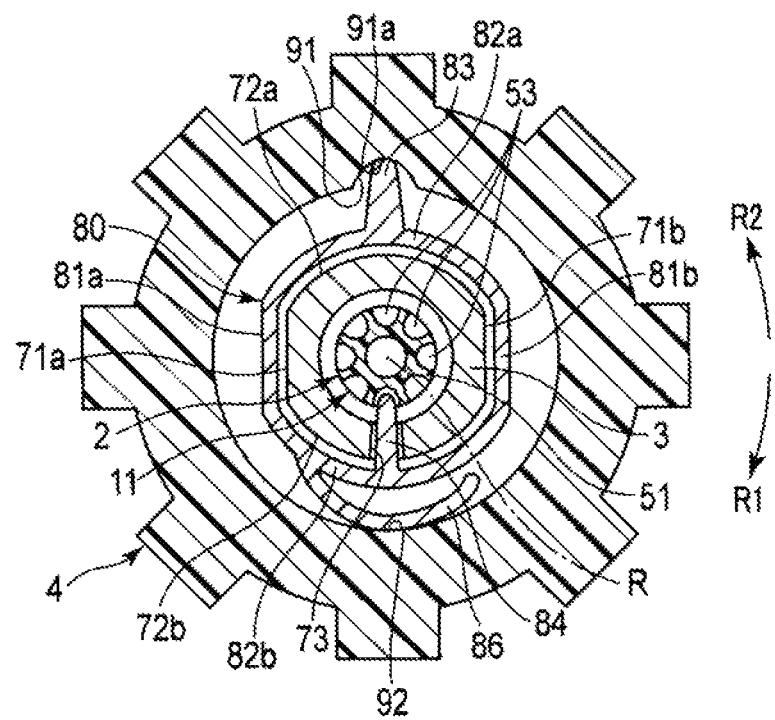
FIG. 5 is a schematic cross-sectional view taken along line IV-IV of FIG. 3, illustrating the manner in which a rotary knob of a treatment tool according to a modification of the first embodiment is not rotated.
Figure 6:
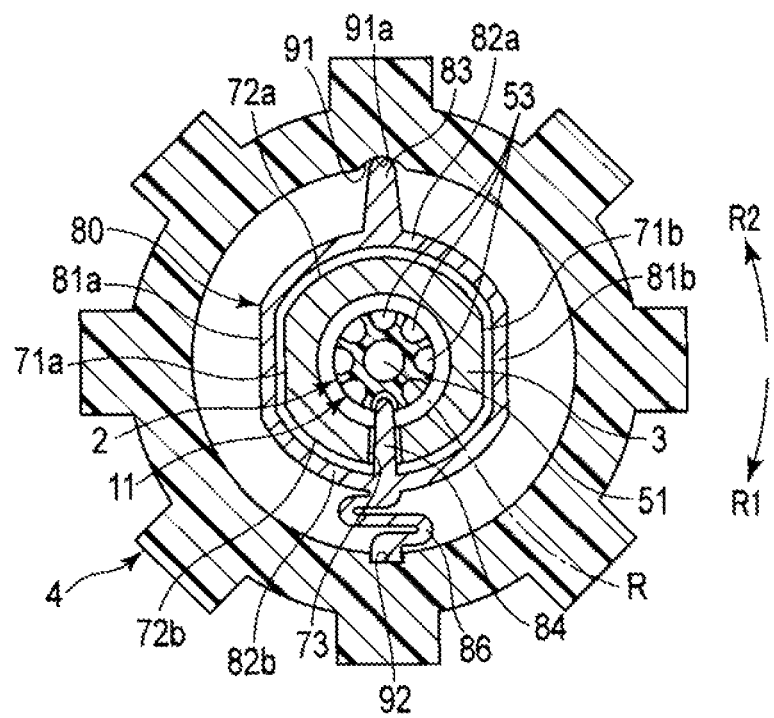
FIG. 6 is a schematic cross-sectional view taken along line IV-IV of FIG. 3, illustrating the manner in which a rotary knob of a treatment tool according to a modification of the first embodiment is not rotated.

A biasing member 86 is disposed between the locking member 80 and the rotary knob 4. The biasing member 86 has an end fixed to the side of the arcuate rod 82b that is opposite the proximal portion of the inner protrusion 84. The biasing member 86 may be a compression helical spring, a leaf spring (not illustrated) or a cylindrical rod of rubber, for example. Alternatively, as illustrated in FIGS. 5 and 6, the biasing member 86 may be made of the same material as and integral with the locking member 80, and may be in the form of a soft resin spring made of a resin. The resin spring as the biasing member 86 is not limited to the shape illustrated in FIGS. 5 and 6, but may be of any of various shapes. The biasing member 86 produces biasing forces for causing the inner protrusion 84 of the locking member 80 to fit into one of the grooves 53 in the housing 2.

As illustrated in FIGS. 3 through 4B, the shaft 3 is prevented from rotating about the predetermined rotational axis R with respect to the locking member 80. The straight rods 81a and 81b of the locking member 80 are longer than the flat faces 71a and 71b of the shaft 3 along directions perpendicular to the predetermined rotational axis R. Consequently, the straight rods 81a and 81b of the locking member 80 are movable in the directions perpendicular to the predetermined rotational axis R along the flat faces 71a and 71b of the shaft 3. The distance that the locking member 80 is movable with respect to the shaft 3 is defined between a position in which the arcuate rod 82a abuts against the arcuate face 72a of the shaft 3 and a position in which the arcuate rod 82b abuts against the arcuate face 72b of the shaft 3. Therefore, the locking member 80 is movable within a predetermined range in the directions perpendicular to the axial directions of the rotational axis R with respect to the shaft 3.

The rotary knob 4 has in an inner circumferential surface thereof a cavity 91 and a fixing portion 92 to which the other end of the biasing member 86 is fixed. The cavity 91 and the fixing portion 92 should preferably face each other. The cavity 91 is substantially V-shaped, for example. The biasing member 86 whose other end is fixed to the fixing portion 92 produces biasing forces that keep a far end portion of the outer protrusion 83 of the locking member 80 in abutment against the cavity 91. Therefore, the outer protrusion 83 of the locking member 80 abuts on the cavity 91, or cam surface, of the rotary knob 4. The cavity 91 of the rotary knob 4 and the outer protrusion 83 of the locking member 80 are kept in abutment against each other at all times. The cavity 91 is shaped as a cam surface for defining a distance that the locking member 80 is movable in the directions perpendicular to the rotational axis R depending on the position where the far end portion of the outer protrusion 83 of the locking member 80 abuts against the cavity 91. In other words, the cavity 91 of the rotary knob 4 defines a range in which the outer protrusion 83 of the locking member 80 is movable in response to rotation of the rotary knob 4 with respect to the housing 2.

When the rotary knob 4 stops being rotated, the outer protrusion 83 of the locking member 80 abuts against and is supported by the bottom 91a, or central portion, of the cavity, or cam surface, as illustrated in FIG. 4A. The bottom 91a is located on the cam surface 91 centrally in the range in which the outer protrusion 83 of the locking member 80 is movable along circumferential directions around the predetermined rotational axis R.

Next, operation of the treatment tool 1 according to the present embodiment will be described below.

In an initial position, or in a state where no rotating force is applied to the rotary knob 4, as illustrated in FIG. 4A, the outer protrusion 83 of the locking member 80 is disposed in a central position, or on the bottom 91a, in the circumferential directions around the predetermined rotational axis R of the cavity 91 of the rotary knob 4. The user of the treatment tool 1, or a surgeon, rotates the rotary knob 4 in the direction indicated by the arrow R1 in FIG. 4A. Then, as illustrated in FIG. 4B, the cavity 91, or cam surface, in the inner circumferential surface of the rotary knob 4 moves the outer protrusion 83 of the locking member 80 toward the predetermined rotational axis R against the biasing forces from the biasing member 86 fixed to the locking member 80. Therefore, the inner protrusion 84 of the locking member 80 moves in a direction away from the predetermined rotational axis R in response to the movement of the outer protrusion 83 of the locking member 80. In other words, the outer protrusion 83, or abutting portion, of the locking member 80 is movable in response to the rotation of the rotary knob 4. The inner protrusion 84 of the locking member 80 is then released from fitting engagement in one of the grooves 53 in the tubular portion 51 of the housing 2. Therefore, based on the relative rotation between the rotary knob 4 and the housing 2, the locking member 80 is released from fitting engagement with the housing 2 against the biasing forces of the biasing member 86, unlocking the shaft 3 from the housing 2 for rotation.

At this time, as illustrated in FIGS. 3 and 4B, the tubular portion 51 of the housing 2 and the proximal-end portion of the shaft 3 have their central axes kept in alignment with the predetermined rotational axis R. Then, an inner circumferential surface of the arcuate rod 82a of the locking member 80 and the arcuate face 72a of the shaft 3 are brought into proximity with each other or into abutment against each other. At this time, the cavity 91 in the inner circumferential surface of the rotary knob 4 and the outer protrusion 83 of the locking member 80 are kept in abutment against each other.

Since the inner protrusion 84 of the locking member 80 is pulled out of the groove 53 in the tubular portion 51 of the housing 2, the housing 2 is unlocked from the locking member 80. The rotary knob 4 illustrated in FIG. 4B is further rotated about the predetermined rotational axis R in the direction indicated by the arrow R1 (see FIG. 4A). As the outer protrusion 83 of the locking member 80 is kept abutting in the cavity 91 in the inner circumferential surface of the rotary knob 4, the shaft 3 fitted in the locking member 80 is rotated in unison with the rotary knob 4. In other words, the rotary knob 4, the locking member 80, and the shaft 3 are rotated together about the predetermined rotational axis R with respect to the tubular portion 51 of the housing 2. Therefore, the rotation of the rotary knob 4 about the predetermined rotational axis R causes the rotary element 6 to rotate about the predetermined rotational axis R in unison with the rotary knob 4.

Therefore, in response to the rotation of the rotary knob 4, the locking member 80 unlocks the shaft 3 from the housing 2 for rotation based on the relative rotation between the rotary knob 4 and the housing 2. In response to the rotation of the rotary knob 4, the locking member 80 rotates the shaft 3 in the same direction as the rotary knob 4.

When the rotary knob 4 is rotated about the predetermined rotational axis R, the shaft 3 is locked by the housing 2 and is not rotated until the inner protrusion 84 of the locking member 80 is pulled out of the groove 53 in the housing 2. Therefore, the rotary knob 4 cooperates with the locking member 80 in forming appropriate play for rotating the rotary knob 4 and the shaft 3. In other words, the cavity 91, or cam surface, of the rotary knob 4 and the outer protrusion 83, or abutting portion, of the locking member 80 define an amount of play until the rotary knob 4 is rotated with respect to the housing 2 to rotate the locking member 80 and the shaft 3 with respect to the housing 2.

The user then takes its hand off the rotary knob 4, stopping the rotary knob 4 from rotation. When the rotation of the rotary knob 4 is stopped, the inner protrusion 84 of the locking member 80 is fitted into one of the grooves 53 in the housing 2 under the biasing forces of the biasing member 86. Even if the distal end of the inner protrusion 84 abuts against the surface between adjacent ones of the grooves 53, the distal end of the inner protrusion 84 slips against the tubular portion 51 under the biasing forces of the biasing member 86, allowing the inner protrusion 84 to be fitted into either one of the grooves 53. In other words, one of the grooves, or fixed fitting portions, of the housing 2 is fitted over the outer protrusion 83, or abutting portion, of the locking member 80 depending on the position thereof. At this time, the rotary knob 4 is appropriately angularly moved due to the play. The inner protrusion 84 of the locking member 80 is thus easily fitted into one of the grooves 53 in the housing 2. Upon stopping of the relative rotation between the rotary knob 4 and the housing 2, the biasing forces of the biasing member 86 are exerted to cause the inner protrusion 84 of the locking member 80 to be fitted into one of the grooves 53 in the housing 2, thereby locking the shaft 3 against rotation with respect to the housing 2. Consequently, the locking member 80 is able to lock the shaft 3 against rotation with respect to the housing 2 upon stopping of the relative rotation between the rotary knob 4 and the housing 2. The outer protrusion 83 of the locking member 80 is moved to the central position in the cavity 91 in the circumferential directions around the predetermined rotational axis R of the cavity 91 under the biasing forces of the biasing member 86. In other words, the biasing member 86 exerts its biasing forces to place the outer protrusion 83 of the locking member 80 in the central portion 91a of the cavity 91 in response to stopping of the relative rotation between the rotary knob 4 and the housing 2.

A load F, or external force, can be applied from a direction off the rotational axis R on the housing 2 to a position on the rotary element 6, i.e., the end effector 5 and/or the shaft 3 that is closer to the distal end of the end effector 5 than the rotary knob 4. Even if a load tending to turn the shaft 3, for example, of the rotary element 6 about the predetermined rotational axis R is applied, the inner protrusion 84 of the locking member 80 remains to be fitted in one of the grooves 53 in the housing 2. Therefore, the shaft 3 and the rotary knob 4 are prevented from rotating of their own accord under the load applied to the rotary element 6 about the predetermined rotational axis R.

While the external force F is imposed on the end effector 5 and/or the shaft 3, the rotary knob 4 can be rotated about the predetermined rotational axis R if the surgeon intends to rotate the rotary knob 4. As illustrated in FIG. 3, the rotary knob 4 has an outer circumferential surface on which the surgeon places its fingers at a position (radius D0>radius D1) that is spaced radially from the predetermined rotational axis R. If the surgeon is to rotate the rotary knob 4 about the predetermined rotational axis R, the surgeon can rotate the rotary knob 4 against the external force F with a small force because of the moment based on the different magnitudes of the radii D0, D1. Therefore, the surgeon can turn the end effector 5, which is positioned off the rotational axis R, for example, around the rotational axis R to push aside a living tissue with the end effector 5, for example.

The example in which the rotary knob 4 is rotated in the direction indicated by the arrow R1 in FIG. 4A has been described above. Another example in which the rotary knob 4 is rotated in the direction indicated by the arrow R2 in FIG. 4A will not be described below as it is different from the above example only as to the direction in which to rotate the rotary knob 4.

As described hereinbefore, the treatment tool 1 according to the present embodiment offers the following advantages:

With the treatment tool 1 according to the present embodiment, even if an external force F is imposed from a direction off the predetermined rotational axis R, for example, the inner protrusion 84 of the locking member 80 that is biased by the biasing member 86 is kept fitted in one of the grooves 53 in the housing 2. In other words, the locking member 80 locks the shaft 3 against rotation with respect to the housing 2. Therefore, the locking member 80 is able to prevent the rotary element 6 from being rotated about the predetermined rotational axis R. Therefore, providing the user does not want to rotate the shaft 3 and the end effector 5 with respect to the housing 2, the user does not need to hold the rotary knob 4 to indirectly prevent the shaft 3 from rotating, but may take its fingers off the rotary knob 4. Consequently, when an external force F is imposed on the end effector 5 that is disposed in a position off the rotational axis R, for example, the locking member 80 is effective to prevent the end effector 5 and the shaft 3 from being rotated about the predetermined rotational axis R in a manner not intended by the surgeon.

On the other hand, if the surgeon intends to rotate the end effector 5 and the shaft 3 about the predetermined rotational axis R, the surgeon may rotate the rotary knob 4 to an extent beyond the play with respect to the locking member 80. The inner protrusion 84 of the locking member 80 that is biased by the biasing member 86 is placed out of fitting engagement in the groove 53 in the housing 2, allowing the shaft 3 fitted in the locking member 80 to rotate. Therefore, the grooves 53, or fixed fitting portions, in the housing 2 are selectively fitted over the inner protrusion 84, or movable fitting portion, of the locking member 80 depending on the position of the inner protrusion 84, thereby preventing the shaft 3 from being rotated with respect to the housing 2 in a selected one of angular positions.

The treatment tool 1 according to the present embodiment is capable of allowing the rotary element 6 to be rotated with respect to the housing 2 if the surgeon intends to rotate the rotary element 6, and is also capable of automatically securing the rotary element 6 to the housing 2 against rotation if the surgeon intends otherwise, or intends not to rotate the rotary element 6.

Modification

Figure 7A:
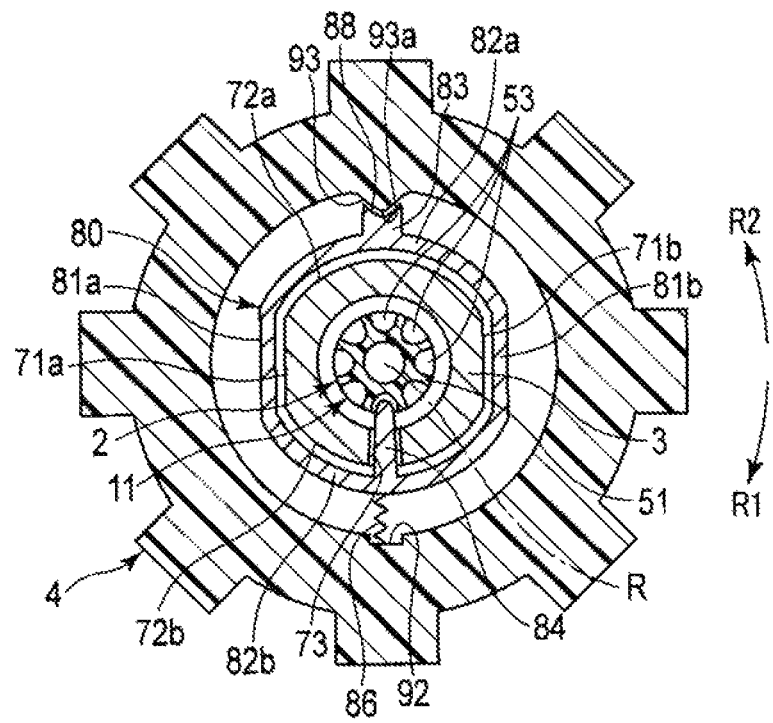
FIG. 7A is a schematic cross-sectional view taken along line IV-IV of FIG. 3, illustrating the manner in which a rotary knob of a treatment tool according to a modification of the first embodiment is not rotated.
Figure 7B:
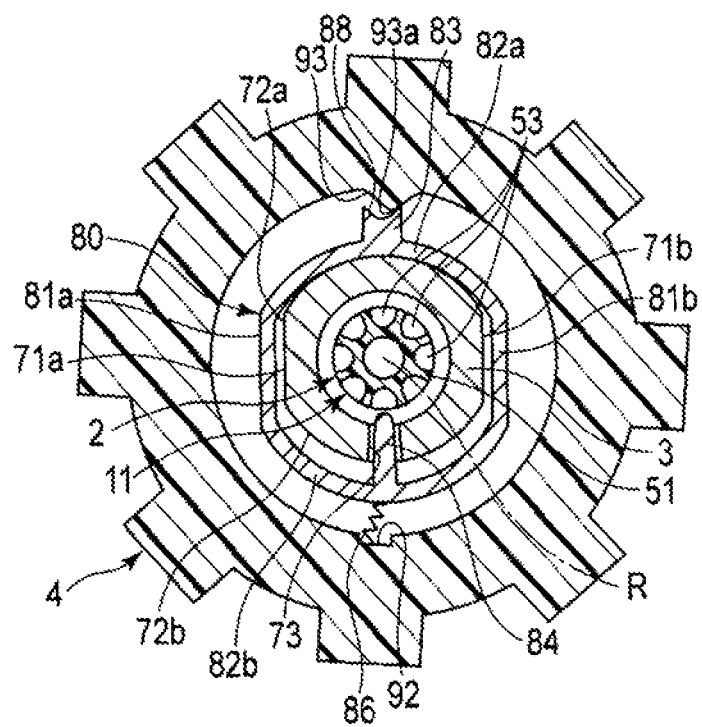
FIG. 7B is a schematic cross-sectional view taken along line IV-IV of FIG. 3, illustrating the manner in which the rotary knob of the treatment tool according to the modification of the first embodiment is rotated about a predetermined rotational axis.

According to the first embodiment, the rotary knob 4 has the cavity 91 defined therein and the locking member 80 has the outer protrusion 83 disposed thereon. Alternatively, as illustrated in FIGS. 7A and 7B, the rotary knob 4 may have a land 93 disposed thereon and the far end portion of the outer protrusion 83 of the locking member 80 may have a cavity 88 defined therein for being fitted over the land 93 of the rotary knob 4. The land 93 of the rotary knob 4 and the cavity 88 in the outer protrusion 83 of the locking member 80 are kept in abutment against each other at all times. The land 93 and the cavity 88 keep the rotary knob 4 and the locking member 80 in the same relationship to each other as with the cavity 91 in the rotary knob 4 and the outer protrusion 83 of the locking member 80, as described hereinbefore.

When the rotary knob 4 stops rotating, as illustrated in FIG. 7A, the outer protrusion 83 of the locking member 80 abuts against and is supported by a central portion 93a of the land 93, or cam surface. The central portion 93a is located on the land 93, or cam surface, centrally in the range in which the cavity 88 in the outer protrusion 83 of the locking member 80 is movable along the circumferential directions around the predetermined rotational axis R.

A second embodiment will be described below with reference to FIGS. 8A through 12. This embodiment is a modification of the first embodiment. Those members which are identical to and which have identical functions to those described in the first embodiment are denoted by as identical numeral references as possible, and will not be described in detail below.

Figure 8A:
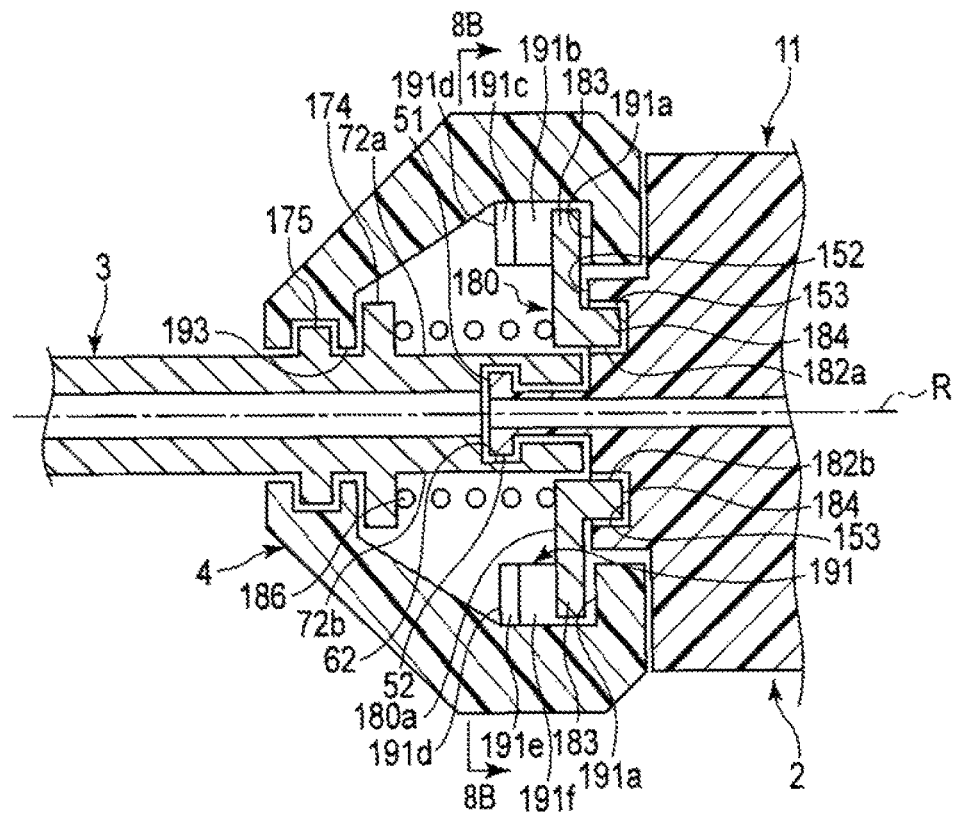
FIG. 8A is a schematic cross-sectional view illustrating an inner configuration of a housing, a rotary knob, and a shaft of a treatment tool according to a second embodiment when the rotary knob and the shaft are not rotated with respect to the housing.
Figure 9A:
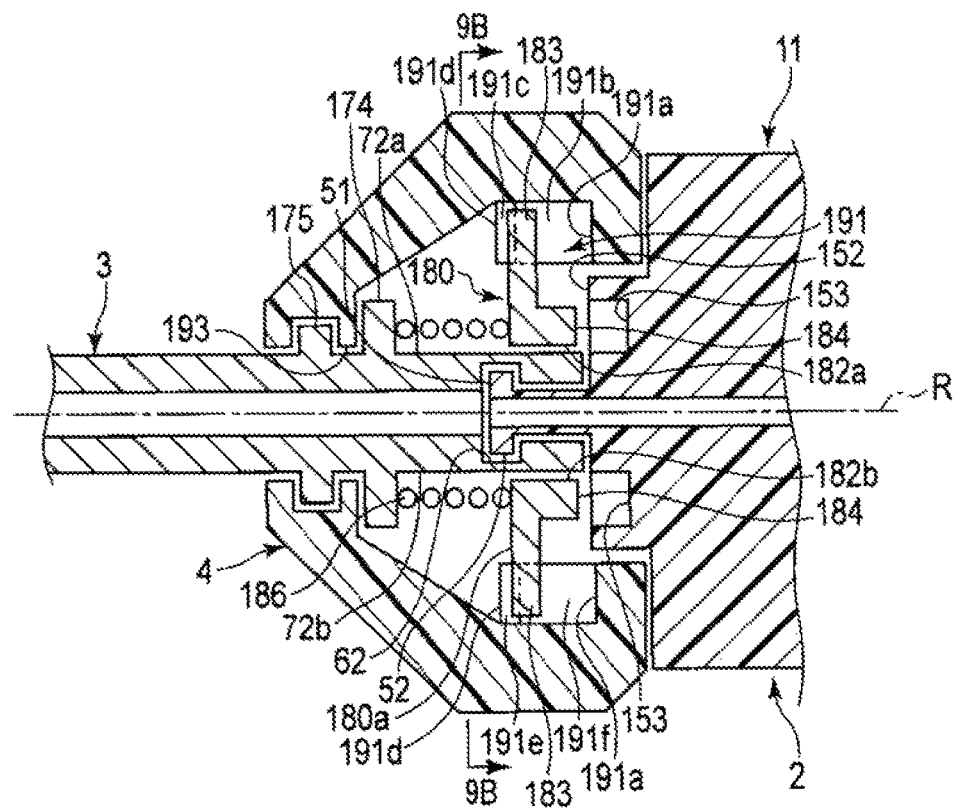
FIG. 9A is a schematic cross-sectional view illustrating an inner configuration of the housing, the rotary knob, and the shaft of the treatment tool according to the second embodiment when the rotary knob and the shaft are rotated about a predetermined rotational axis with respect to the housing.

As illustrated in FIGS. 8A and 9A, the tubular portion 51 on the distal-end portion of the housing 2 has the fitting portion 52 disposed thereon. The shaft 3 has the fitting portion 62, or fitting recess in the illustrated embodiment, defined in the inner circumferential surface of the proximal-end portion thereof and fitted over the fitting portion 52 of the housing 2. The fitting portion 52 on the distal-end portion of the housing 2 that is fitted in the fitting portion 62 in the proximal-end portion of the shaft 3 allows the shaft 3 to rotate about the predetermined rotational axis R while preventing the shaft 3 from moving along the predetermined rotational axis R with respect to the housing 2.

The housing 2 has a protruding face 152 on a region thereof that is closer to the proximal-end side than the tubular portion 51 on the distal-end portion of the housing 2. The protruding face 152 protrudes radially outwardly away from the predetermined rotational axis R beyond the tubular portion 51. The protruding face 152 has a plurality of holes, or fixed fitting portions, defined therein. The holes 153 should preferably extend parallel to the predetermined rotational axis R. A protrusion 184, or movable fitting portion, (see FIG. 11) of a locking member 180 to be described hereinafter is fitted in one or more of the holes 153.

The shaft 3 has the pair of flat faces 71a and 71b and the pair of arcuate faces 72a and 72b on the outer circumferential surface of the proximal-end portion thereof. The shaft 3 has an outer flange 174 projecting radially outwardly away from the rotational axis R at an outer circumferential surface of the proximal-end portion thereof that is closer to the distal-end side than the flat faces 71a and 71b and the arcuate faces 72a and 72b. The outer flange 174 of the shaft 3 supports a biasing member 186 in cooperation with a face or face side of an annular portion 180a, to be described hereinafter, of the locking member 180. The shaft 3 also has an outer flange 175 projecting radially outwardly away from the rotational axis R at a position that is closer to the distal-end side than the outer flange 174. The outer flange 175 functions as a fitting portion fitted in the rotary knob 4.

The rotary knob 4 has a fitting portion 193 supported between the outer flanges 174 and 175. The fitting portion 193 prevents the shaft 3 from being moved along the predetermined rotational axis R with respect to the housing 2. The fitting portion 193 also prevents the rotary knob 4 from being moved along the predetermined rotational axis R with respect to the housing 2.

The locking member 180 is fitted over the outer circumferential surface of the proximal-end portion of the shaft 3. The locking member 180 has an annular portion 180a, or main body, fitted over the proximal-end portion of the shaft 3 and a pair of outer protrusions 183, or abutting portions, protruding from the annular portion 180a radially outwardly away from the predetermined rotational axis R. The outer protrusions 183 should preferably be integral with the annular portion 180a. The outer protrusions 183 of the locking member 180 protrude from an outer circumferential surface of the annular portion 180a, or main body, radially outwardly away from the predetermined rotational axis R.

Figure 11:
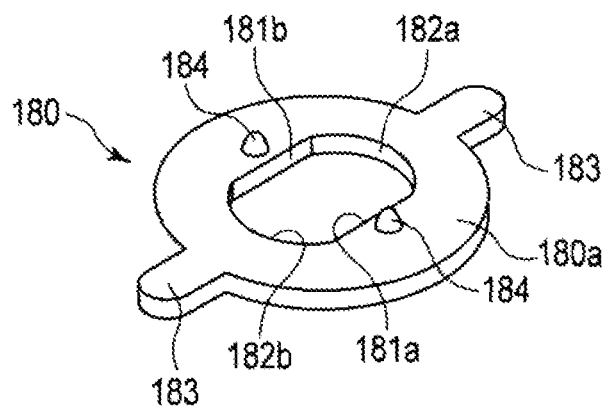
FIG. 11 is a schematic perspective view of the locking member of the treatment tool according to the second embodiment, as viewed from a side opposite the side illustrated in FIG. 10.
Figure 12:
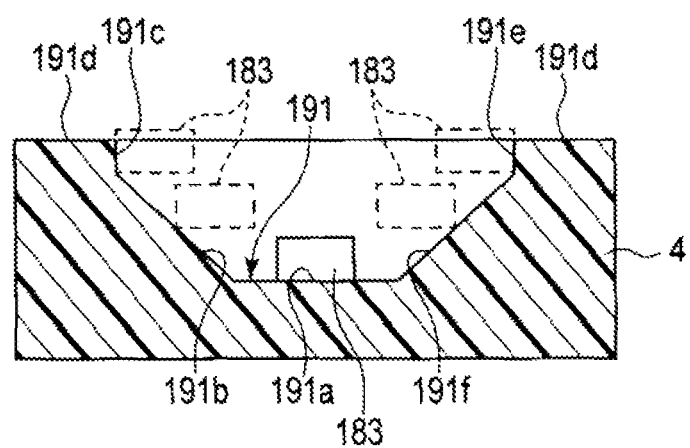
FIG. 12 is a schematic cross-sectional view taken along line XII-XII of FIGS. 8B and 9B.

As illustrated in FIGS. 8A and 9A, and 11, the annular portion 180a of the locking member 180 has protrusions 184 on a face, or reverse side, thereof that faces the protruding face 152 of the housing 2. The protrusions 184 can be fitted in the holes 153 in the protruding face 152 of the housing 2. The number of the protrusions 184 on the annular portion 180a of the locking member 180 is smaller than the number of the holes 153 in the protruding face 152 of the housing 2. If there are a plurality of protrusions 184, then all of the protrusions 184 are fitted in either ones of the holes 153.

The annular portion 180a of the locking member 180 has a pair of flat face portions 181a and 181b and a pair of arcuate faces 182a and 182b on an inner side thereof. The flat face portions 181a and 181b should preferably lie parallel to each other. The arcuate faces 182a and 182b should preferably be part of arcs around the predetermined rotational axis R of the shaft 3. The flat face portions 181a and 181b of the locking member 180 are slightly longer than the flat faces 71a and 72b of the shaft 3 in directions perpendicular to the predetermined rotational axis R. The radii of the arcuate faces 182*a* and 182*b* of the locking member 180 from the rotational axis R are slightly larger than the radii of the arcuate faces 72*a* and 72*b* of the shaft 3. The flat face 71*a* of the shaft 3 faces the flat face portion 181*a* of the annular portion 180*a*. The flat face 71*b* of the shaft 3 faces the flat face portion 181*b* of the annular portion 180*a*. The arcuate face 72*a* of the shaft 3 faces the arcuate face 182*a* of the annular portion 180*a*. The arcuate face 72*b* of the shaft 3 faces the arcuate face 182*b* of the annular portion 180*a*. Therefore, the locking member 180 is fitted over the outer circumferential surface of the proximal-end portion of the shaft 3. In other words, the shaft 3 is prevented from being rotated about the predetermined rotational axis R with respect to the locking member 180. Though the locking member 180 is movable along the predetermined rotational axis R with respect to the shaft 3, the locking member 180 is prevented from being rotated about the predetermined rotational axis R with respect to the shaft 3. Therefore, the locking member 180 is movable along the predetermined rotational axis R with respect to the outer circumferential surface of the shaft 3.

The biasing member 186 is disposed between the locking member 180 and the shaft 3. The biasing member 186 has an end supported by the outer flange 174 of the shaft 3, for example, and another end supported by the annular portion 180*a* of the locking member 180. The biasing member 186 may be a compression helical spring or a cylindrical or tubular member of rubber, for example. The biasing member 186 exerts biasing forces tending to cause the protrusions 184 on the locking member 180 to be fitted into the holes 153 in the housing 2.

As illustrated in FIGS. 8A through 12, the rotary knob 4 has a cam surface 191 on a proximal-end portion thereof. The cam surface 191 extends circumferentially around the predetermined rotational axis R and is directed radially inwardly. The outer protrusions 183 of the locking member 180 are held in abutment against the cam surface 191 under the biasing forces of the biasing member 186. Therefore, the outer protrusions 183 of the locking member 180 are abutted by the cam surface 191 of the rotary knob 4. The cam surface 191 of the rotary knob 4 and the outer protrusions 183 of the locking member 180 are kept in abutment against each other at all times. The cam surface 191 defines a distance by which to move the locking member 180 in directions along the rotational axis R depending on the position where far end portions of the outer protrusions 183 of the locking member 180 abut against the cam surface 191. In other words, the cam surface 191 of the rotary knob 4 defines a range in which the outer protrusions 183 of the locking member 180 are movable in response to rotation of the rotary knob 4 with respect to the housing 2.

The cam surface 191 has a pair of cavities 191*a*, a pair of first slanted faces 191*b*, a pair of first limiting faces 191*c*, a pair of lands 191*d*, a pair of second limiting faces 191*e*, and a pair of second slanted faces 191*f*. The first limiting faces 191*c*, the lands 191*d*, the second limiting faces 191*e*, and the second slanted faces 191*f* in each pair are disposed in symmetric positions across the predetermined rotational axis R. The cavities 191*a*, the first slanted faces 191*b*, the first limiting faces 191*c*, the lands 191*d*, the second limiting faces 191*e*, and the second slanted faces 191*f* jointly make up a continuous annulus.

The cavities 191*a* are defined by flat faces, for example. The flat faces that define the cavities 191*a* lie on a plane perpendicular to the predetermined rotational axis R. The first slanted faces 191*b* are adjacent to the cavities 191*a* in the circumferential directions around the rotational axis R.

The first slanted faces 191*b* protrude progressively toward the distal-end side along the rotational axis R as they are progressively spaced apart from the cavities 191*a* along the circumferential directions around the rotational axis R. The first limiting faces 191*c* are adjacent to the first slanted faces 191*b* in the circumferential directions around the rotational axis R. The first limiting faces 191*c* protrude toward the distal-end side along the rotational axis R and are defined as flat faces parallel to the rotational axis R, for example. The lands 191*d* are adjacent to the first limiting faces 191*c* in the circumferential directions around the rotational axis R. The lands 191*d* are defined as flat faces, for example. In this case, the lands 191*d* lie perpendicularly to the first limiting faces 191*c*. The lands 191*d* are disposed on a plane perpendicular to the predetermined rotational axis R. The second limiting faces 191*e* are adjacent to the lands 191*d* in the circumferential directions around the rotational axis R. The second limiting faces 191*e* protrude a reduced distance along the rotational axis R and are defined as flat faces parallel to the rotational axis R, for example. The second slanted faces 191*f* are adjacent to the second limiting faces 191*e* in the circumferential directions around the rotational axis R. The second slanted faces 191*f* protrude a progressively smaller distance along the rotational axis R as they are progressively spaced apart from the second limiting faces 191*e* along the circumferential directions around the rotational axis R. The second slanted faces 191*f* are adjacent to the cavities 191*a*.

Figure 8B:
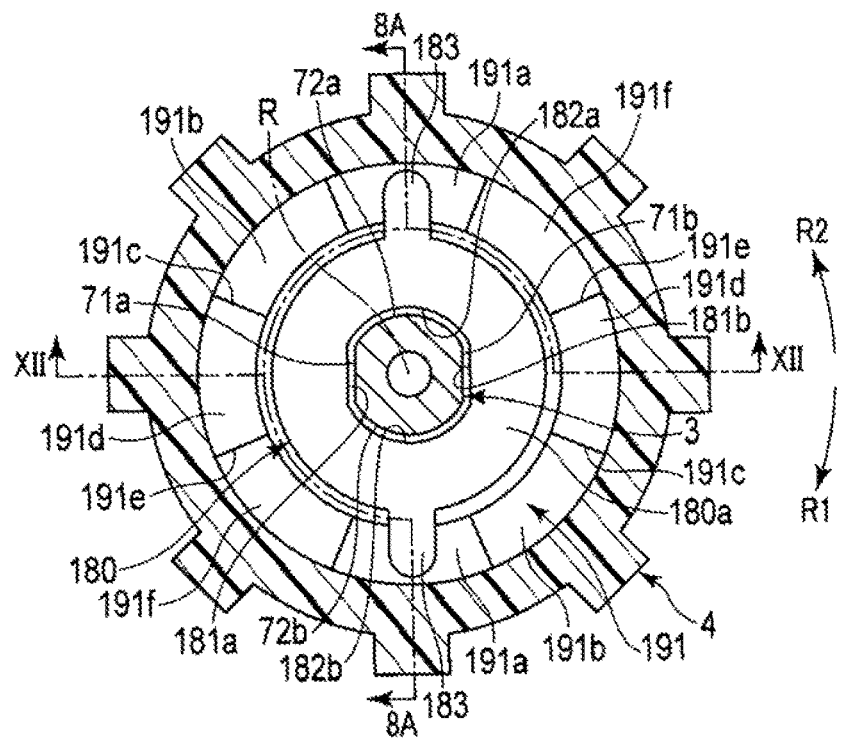
FIG. 8B is a schematic cross-sectional view taken along line 8B-8B of FIG. 8A, illustrating the manner in which the rotary knob of the treatment tool according to the second embodiment is not rotated.
Figure 9B:
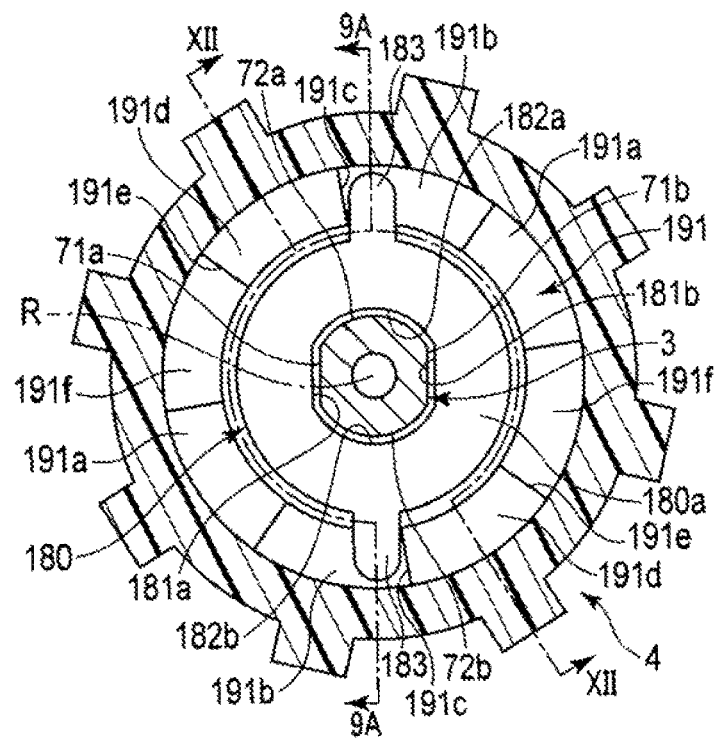
FIG. 9B is a schematic cross-sectional view taken along line 9B-9B of FIG. 9A, illustrating the manner in which the rotary knob of the treatment tool according to the second embodiment is rotated about the predetermined rotational axis.
Figure 10:
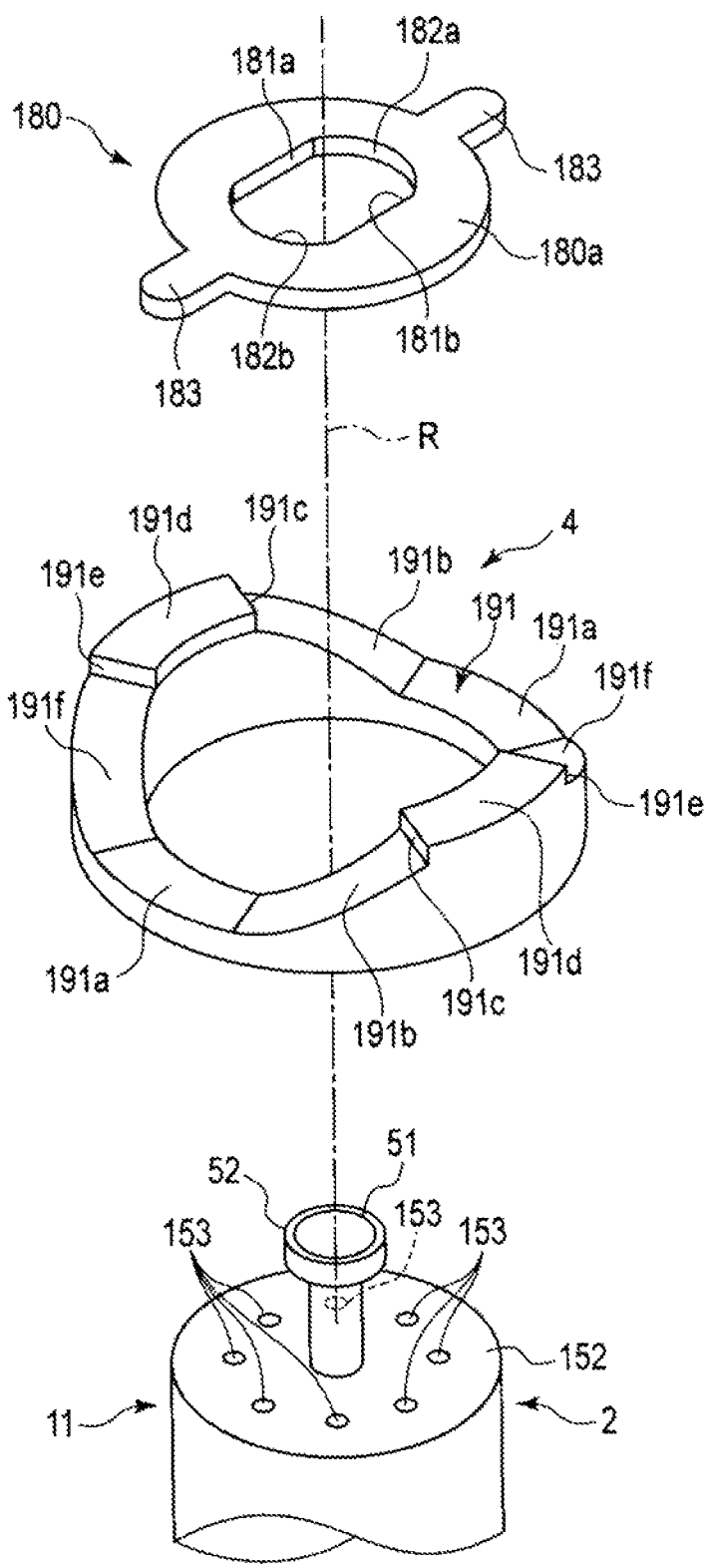
FIG. 10 is a schematic exploded perspective view of the housing, the rotary knob, and a locking member of the treatment tool according to the second embodiment.

As illustrated in FIGS. 8B and 9B, the cavities 191*a*, the first slanted faces 191*b*, the first limiting faces 191*c*, the lands 191*d*, the second limiting faces 191*e*, and the second slanted faces 191*f* have inner circumferential surfaces spaced by appropriate gaps from outer circumferential surfaces of the annular portion 180*a* of the locking member 180. When the rotary knob 4 is not rotated about the predetermined rotational axis R, as illustrated in FIGS. 8A and 8B, the outer protrusions 183 of the locking member 180 are placed in the cavities 191*a* under the biasing forces of the biasing members 186.

When the rotary knob 4 stops rotating, as illustrated in FIGS. 8A and 8B, the outer protrusions 183 of the locking member 180 abut against and are supported by the cavities 191*a*, or central portions, of the cam surface 191. The cavities 191*a* are defined in the cam surface 191 centrally in the ranges in which the outer protrusions 183 of the locking member 180 are movable along the circumferential directions around the predetermined rotational axis R.

Next, operation of the treatment tool 1 according to the present embodiment will be described below.

In an initial position, or in a state where no rotating force is applied to the rotary knob 4, as illustrated in FIG. 8B, the outer protrusions 183 of the locking member 180 are disposed on the cam surface 191 of the rotary knob 4 in the central positions, or cavities 191*a*, in the circumferential directions around the predetermined rotational axis R. The user of the treatment tool 1, or the surgeon, rotates the rotary knob 4 in the direction indicated by the arrow R1 in FIG. 8B. The locking member 180 is allowed to move in the axial directions of the rotational axis R with respect to the shaft 3, but is prevented from rotating with respect to the shaft 3. Therefore, as illustrated in FIGS. 9A and 9B, as the cam surface 191 of the rotary knob 4, which is in the state in which the outer protrusions 183 of the locking member 180 is placed in the cavities 191*a*, is rotated about the rotational axis R, the first slanted faces 191*b* adjacent to the cavities 191*a* move the outer protrusions 183 of the locking member 180 from the cavities 191*a* toward the distal-end side along the rotational axis R. Specifically, the first slanted faces 191*b* move the outer protrusions 183 of the locking member 180 toward the distal-end side along the predetermined rotational axis R against the biasing forces of the biasing member 186 of the locking member 180. In response to the movement of the outer protrusions 183 of the locking member 180, the protrusions 184 of the locking member 180 are moved in a direction away from the holes 153 in the protruding face 152 of the housing 2. The protrusions 184 of the locking member 180 are released out of fitting engagement in the holes 153 in the protruding face 152 of the housing 2. Therefore, based on the relative rotation between the rotary knob 4 and the housing 2, the locking member 180 is released from fitting engagement with the housing 2 against the biasing forces of the biasing member 186, unlocking the shaft 3 from the housing 2 for rotation.

At this time, the tubular portion 51 of the housing 2 and the proximal-end portion of the shaft 3 have their central axes kept in alignment with the predetermined rotational axis R. At this time, the cam surface 191 on the inner circumferential surface of the rotary knob 4 and the outer protrusions 183 of the locking member 180 are kept in abutment against each other.

Since the protrusions 184 of the locking member 180 are pulled out of the holes 153 in the tubular portion 51 of the housing 2, the housing 2 is unlocked from the locking member 180. The surgeon further rotates the rotary knob 4 illustrated in FIG. 9B in the direction indicated by the arrow R1 (see FIG. 8B) about the predetermined rotational axis R. As the cam surface 191 on the inner circumferential surface of the rotary knob 4 and the outer protrusions 183 of the locking member 180 are kept in abutment against each other, the shaft 3 fitted in the locking member 180 is rotated together with the rotary knob 4. In other words, the rotary knob 4, the locking member 180, and the shaft 3 are rotated all together about the predetermined rotational axis R with respect to the tubular portion 51 of the housing 2. Therefore, when the rotary knob 4 is rotated about the predetermined rotational axis R, the rotary element 6 is rotated in unison therewith about the predetermined rotational axis R.

Specifically, in response to the rotation of the rotary knob 4, the locking member 180 releases the shaft 3 from the housing 2 for rotation depending on the relative rotation between the rotary knob 4 and the housing 2. The shaft 3 is allowed to rotate in the same direction as the rotary knob 4 in response to the rotation of the rotary knob 4.

Depending on the speed at which, and the extent to which, the rotary knob 4 is rotated with respect to the housing 2, the outer protrusions 183 of the locking member 180 are brought into abutment against the first limiting faces 191*c*.

When the rotary knob 4 is rotated about the predetermined rotational axis R, until the protrusions 184 of the locking member 180 are pulled out of the holes 153 in the housing 2, since the housing 2 and the shaft 3 are locked together, the shaft 3 is not rotated. Therefore, the rotary knob 4 cooperates with the locking member 180 in forming appropriate play for rotating the rotary knob 4 and the shaft 3. In other words, the cam surface 191 of the rotary knob 4 and the outer protrusions 183, or abutting portions, of the locking member 180 define an amount of play until the rotary knob 4 is rotated with respect to the housing 2 to rotate the locking member 180 and the shaft 3 with respect to the housing 2.

The user then takes its hand off the rotary knob 4, stopping the rotary knob 4 from rotation. When the rotation of the rotary knob 4 is stopped, the protrusions 184 of the locking member 180 move toward the holes 153 in the protruding face 152 under the biasing forces of the biasing member 186. The protrusions 184 of the locking member 180 are then fitted into the holes 153 in the housing 2. Even if the protrusions 184 abut against the surface between adjacent ones of the holes 153, the protrusions 184 slip against the protruding face 152 under the biasing forces of the biasing member 186, allowing the protrusions 184 to be fitted into either ones of the holes 153. In other words, the holes, or fixed fitting portions, in the housing 2 are fitted over the outer protrusions 183, or movable fitting portions, of the locking member 180 depending on the positions thereof. At this time, the rotary knob 4 is appropriately angularly moved due to the play. The protrusions 184 of the locking member 180 are thus easily fitted into some of the holes 153 in the housing 2. Upon stopping of the relative rotation between the rotary knob 4 and the housing 2, the biasing forces of the biasing member 186 are exerted to cause the protrusions 184 of the locking member 180 to be fitted into some of the holes 153 in the housing 2, thereby locking the shaft 3 against rotation with respect to the housing 2. Consequently, the locking member 180 is able to lock the shaft 3 against rotation with respect to the housing 2 upon stopping of the relative rotation between the rotary knob 4 and the housing 2. The outer protrusions 183 of the locking member 180 are moved into the cavities 191*a*, or central portions, of the cam surface 191 under the biasing forces of the biasing member 186. In other words, the biasing member 186 exerts its biasing forces to place the outer protrusions 183 of the locking member 180 in the cavities 191*a*, or central portions, of the cam surface 191 in response to stopping of the relative rotation between the rotary knob 4 and the housing 2.

A load F, or external force, can be applied from a direction off the rotational axis R on the housing 2 to a position on the rotary element 6, i.e., the end effector 5 and/or the shaft 3 that is closer to the distal end of the end effector 5 than the rotary knob 4. Even if a load tending to turn the shaft 3, for example, of the rotary element 6 about the predetermined rotational axis R is applied, the protrusions 184 of the locking member 180 remain to be fitted in some of the holes 153 in the housing 2. Therefore, the shaft 3 and the rotary knob 4 are prevented from rotating of their own accord under the load applied to the rotary element 6 about the predetermined rotational axis R.

While the external force F is imposed on the end effector 5 and/or the shaft 3, the rotary knob 4 can be rotated about the predetermined rotational axis R if the surgeon intends to rotate the rotary knob 4. If the surgeon is to rotate the rotary knob 4 about the predetermined rotational axis R, the surgeon can rotate the rotary knob 4 against the external force F. Therefore, the surgeon can turn the end effector 5, which is positioned off the rotational axis R, for example, around the rotational axis R to push aside a living tissue with the end effector 5, for example.

The example in which the rotary knob 4 is rotated in the direction indicated by the arrow R1 in FIG. 8B has been described above. Another example in which the rotary knob 4 is rotated in the direction indicated by the arrow R2 in FIG. 8B will not be described below as it is different from the above example only as to the direction in which to rotate the rotary knob 4.

As described hereinbefore, the treatment tool 1 according to the present embodiment offers the following advantages:

With the treatment tool 1 according to the present embodiment, even if an external force F is imposed from a direction off the predetermined rotational axis R, for example, the protrusions 184 of the locking member 180 that is biased by the biasing member 186 is kept fitted in some of the holes 153 in the housing 2. In other words, the locking member 180 locks the shaft 3 against rotation with respect to the housing 2. Therefore, the locking member 180 is able to prevent the rotary element 6 from being rotated about the predetermined rotational axis R. Therefore, providing the user does not want to rotate the shaft 3 and the end effector 5 with respect to the housing 2, the user does not need to hold the rotary knob 4 to indirectly prevent the shaft 3 from rotating, but may take its fingers off the rotary knob 4. Consequently, when an external force F is imposed on the end effector 5 that is disposed in a position off the rotational axis R, for example, the locking member 180 is effective to prevent the end effector 5 and the shaft 3 from being rotated about the predetermined rotational axis R in a manner not intended by the surgeon.

On the other hand, if the surgeon intends to rotate the end effector 5 and the shaft 3 about the predetermined rotational axis R, the surgeon may rotate the rotary knob 4 to an extent beyond the play with respect to the locking member 180. The protrusion 184 of the locking member 180 that is biased by the biasing member 186 are placed out of fitting engagement in the holes 153 in the housing 2, allowing the shaft 3 fitted in the locking member 180 to rotate.

The treatment tool 1 according to the present embodiment is capable of allowing the rotary element 6 to be rotated with respect to the housing 2 if the surgeon intends to rotate the rotary element 6, and is also capable of automatically securing the rotary element 6 to the housing 2 against rotation if the surgeon intends otherwise, or intends not to rotate the rotary element 6.

Figure 13A:
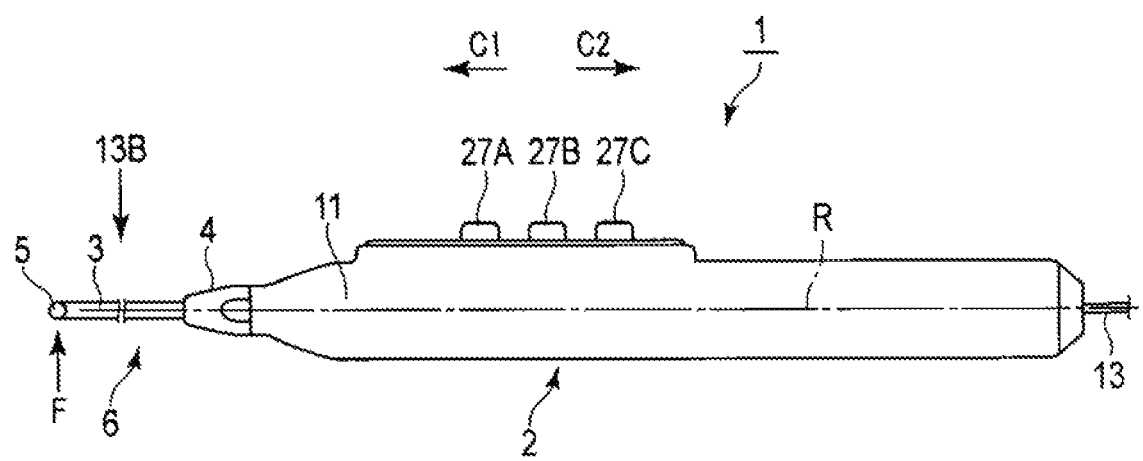
FIG. 13A is a schematic view illustrating a treatment tool according to a third embodiment.
Figure 13B:
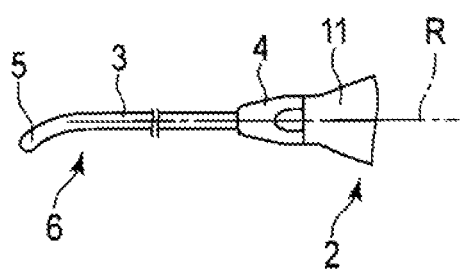
FIG. 13B is a schematic view illustrating a rotary element and a rotary knob as viewed in a direction indicated by the arrow 13B in FIG. 13A.

A third embodiment will be described below with reference to FIGS. 13A and 13B. This embodiment is a modification of the first and second embodiments. Those members which are identical to and which have identical functions to those described in the first and second embodiments are denoted by as identical numeral references as possible, and will not be described in detail below.

According to the first and second embodiments, the example in which the end effector 5 is actively movable on the distal end of the shaft 3 has been described. The example in which the gripping members 16 and 17 (see FIGS. 1 and 2) of the end effector 5 are openable and closable relatively to each other has been described. An example in which an end effector 5 is integral with the distal end of a shaft 3 and is curved with respect to the shaft 3 will be described below. According to the present embodiment, specifically, the end effector 5 is curved with respect to the shaft 3 and extends therefrom at a position off a predetermined rotational axis R.

According to the present embodiment, manipulating buttons 27A, 27B, and 27C are mounted on the housing body 11 of the housing 2. When each of the manipulating buttons 27A, 27B, and 27C is pressed, it enters a manipulation. When each of the manipulating buttons 27A, 27B, and 27C enters a manipulation, the treatment tool 1 is operated in a predetermined operation mode. At this time, as with known treatment tools, any of a high-frequency current, ultrasonic vibrations, and heater-generated head is applied as a treatment energy to a treatment target that is held in contact with the end effector 5.

When an external force F (see FIG. 13A) is imposed on the rotary element 6, for example, the rotary element 6 is prevented from rotating with respect to the housing 2. Therefore, when the external force F is imposed on the end effector 5 that is disposed in a position off the predetermined rotational axis R, for example, the locking member 80 is effective to prevent the end effector 5 and the shaft 3 from being rotated about the predetermined rotational axis R in a manner not intended by the surgeon.

On the other hand, if the surgeon is to manipulate the rotary knob 4, the surgeon can rotate the rotary knob 4 in order to push aside a living tissue with the end effector 5, for example, against frictional forces between the housing 2 and the rotary knob 4 under a rotary moment about the predetermined rotational axis R.

One aspect of the disclosed technology is directed to a treatment tool comprises a housing and a rotary element configured to be attached to the housing so as to define the treatment tool for treating an examinee. The rotary element is defined by an elongated member being rotatable about a rotational axis with respect to the housing. A rotary member is attached to the elongated member to rotate the elongated member. An end effector is attached to the elongated member. The rotary member is disposed coaxially with the elongated member and rotatable with respect to the housing. A locking member is used for unlocking the elongated member from the housing for rotation depending on relative rotation between the rotary member and the housing in response to rotation of the rotary member to allow the elongated member to rotate in the same direction as the rotary member in response to rotation of the rotary member and locking the elongated member against rotation with respect to the housing upon stopping of relative rotation between the rotary member and the housing. The elongated member is prevented from being rotated about the rotational axis with respect to the locking member. The rotary member includes a cam surface defining a range in which the locking member is movable depending on rotation of the rotary member with respect to the housing. The locking member has a biasing member exerting biasing forces tending to cause the locking member to be fitted in the housing and an abutting portion abutted by the cam surface of the rotary member. The cam surface has a central portion disposed centrally in the range. The biasing member exerts the biasing forces thereof upon stopping of relative rotation between the rotary member and the housing to place the abutting portion of the locking member on the central portion.

The locking member has a movable fitting portion movable in response to rotation of the rotary member. The housing has a fitting portion for selecting a position in which the elongated member is prevented from rotating with respect to the housing due to a selected state in which the housing is fitted over the movable fitting portion of the locking member depending on the position of the movable fitting portion. The locking member is movable along an axial direction of the rotational axis with respect to the elongated member. The locking member is movable perpendicularly to an axial direction of the rotational axis with respect to the elongated member. The cam surface and the abutting portion together define a movement until the rotary member is rotated with respect to the housing so as to rotate the locking member and the elongated member with respect to the housing. The locking member is released from fitting engagement with the housing for rotation against the biasing forces of the biasing member depending on relative rotation between the rotary member and the housing, to unlock the elongated member from the housing for rotation, and the locking member is fitted into the housing to lock the elongated member against rotation with respect to the housing under the biasing forces of the biasing member upon stopping of relative rotation between the rotary member and the housing. The end effector is disposed in a position off the rotational axis. The end effector is bendable with respect to the elongated member.

Another aspect of the disclosed technology is directed to a treatment tool comprises a housing and a rotary element configured to be attached to the housing so as to define the treatment tool for treating an examinee. The rotary element is defined by an elongated member being rotatable about a rotational axis with respect to the housing. A rotary member is attached to the elongated member to rotate the elongated member. An end effector is attached to the elongated member. The rotary member is disposed coaxially with the elongated member and rotatable with respect to the housing. A locking member is used for unlocking the elongated member from the housing for rotation depending on relative rotation between the rotary member and the housing in response to rotation of the rotary member, to allow the elongated member to rotate in the same direction as the rotary member in response to rotation of the rotary member, and locking the elongated member against rotation with respect to the housing upon stopping of relative rotation between the rotary member and the housing. The rotary member includes a cam surface defining a range in which the locking member is movable depending on rotation of the rotary member with respect to the housing. The locking member has an abutting portion abutted by the cam surface of the rotary member. The cam surface and the abutting portion together define a movement until the rotary member is rotated with respect to the housing so as to rotate the locking member and the elongated member with respect to the housing.

The locking member has a movable fitting portion movable in response to rotation of the rotary member. The housing has a fitting portion for selecting a position in which the elongated member is prevented from rotating with respect to the housing due to a selected state in which the housing is fitted over the movable fitting portion of the locking member depending on the position of the movable fitting portion. The elongated member is prevented from being rotated about the rotational axis with respect to the locking member. The locking member is movable along an axial direction of the rotational axis with respect to the elongated member. The locking member is movable perpendicularly to an axial direction of the rotational axis with respect to the elongated member. The locking member has a biasing member exerting biasing forces tending to cause the locking member to be fitted in the housing. The cam surface has a central portion disposed centrally in the range and the biasing member exerts the biasing forces thereof upon stopping of relative rotation between the rotary member and the housing to place the abutting portion of the locking member on the central portion. The locking member has a biasing member exerting biasing forces tending to cause the locking member to be fitted in the housing. The locking member is released from fitting engagement with the housing for rotation against the biasing forces of the biasing member depending on relative rotation between the rotary member and the housing, to unlock the elongated member from the housing for rotation, and the locking member is fitted into the housing to lock the elongated member against rotation with respect to the housing under the biasing forces of the biasing member upon stopping of relative rotation between the rotary member and the housing. The end effector is disposed in a position off the rotational axis and is bendable with respect to the elongated member.

A further aspect of the disclosed technology is directed to a treatment tool comprises a housing and an elongated member having a proximal-end side and a distal-end side. The proximal-end side is attached to the housing. The distal-end side attaching to an end effector treating an examinee. The elongated member is rotatable about a rotational axis with respect to the housing. A rotary member is disposed coaxially with the elongated member. The rotary member is rotatable with respect to the housing. The rotary member is configured to rotate the shaft. The rotary member having a cam surface and the cam surface having a central portion. A locking member is configured to lock the elongated member with respect to the housing. The locking member is configured to unlock the elongated member from the housing by being added a rotational power beyond a limit to the rotary member. The locking member includes a biasing member and an abutting portion. The biasing member is configured to exert biasing forces so as to cause the locking member to be fitted in the housing. The abutting portion is abutted by the cam surface of the rotary member. The biasing member is configured to exert the biasing forces to place the abutting portion on the central portion of the cam surface when the rotary member is not rotated. The housing has an immovable fitting portion and the locking member has a movable fitting portion movable in response to rotation of the rotary member. The movable fitting portion fitting to the immovable fitting portion so that the elongated member is not rotatable with respect to the housing. The movable fitting portion not fitting to the immovable fitting portion so that the elongated member is rotatable with respect to the housing. The cam surface and the abutting portion together define a movement until the rotary member is rotated with respect to the housing to rotate the locking member and the shaft with respect to the housing.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A treatment tool comprising:
a housing; and
a rotary element configured to be attached to the housing so as to define the treatment tool for treating an examinee wherein the rotary element is defined by
an elongated member being rotatable about a rotational axis with respect to the housing,
a rotary member being attached to the elongated member to rotate the elongated member, and
an end effector being attached to the elongated member;
the rotary member being disposed coaxially with the elongated member and rotatable with respect to the housing; and
a locking member being used for unlocking the elongated member from the housing for rotation depending on relative rotation between the rotary member and the housing in response to rotation of the rotary member, to allow the elongated member to rotate in the same direction as the rotary member in response to rotation of the rotary member and locking the elongated member against rotation with respect to the housing upon stopping of relative rotation between the rotary member and the housing,
wherein
the elongated member is prevented from being rotated about the rotational axis with respect to the locking member,
the rotary member includes a cam surface defining a range in which the locking member is movable depending on rotation of the rotary member with respect to the housing,
the locking member has a biasing member exerting biasing forces tending to cause the locking member to be fitted in the housing and an abutting portion abutted by the cam surface of the rotary member,
the cam surface has a central portion disposed centrally in the range, and
the biasing member exerts the biasing forces thereof upon stopping of relative rotation between the rotary member and the housing to place the abutting portion of the locking member on the central portion.

2. The treatment tool of claim 1, wherein the locking member has a movable fitting portion movable in response to rotation of the rotary member, and
the housing has a fitting portion for selecting a position in which the elongated member is prevented from rotating with respect to the housing, due to a selected state in which the housing is fitted over the movable fitting portion of the locking member depending on the position of the movable fitting portion.

3. The treatment tool of claim 1, wherein the locking member is movable along an axial direction of the rotational axis with respect to the elongated member.

4. The treatment tool of claim 1, wherein the locking member is movable perpendicularly to an axial direction of the rotational axis with respect to the elongated member.

5. The treatment tool of claim 1, wherein
the cam surface and the abutting portion together define a movement until the rotary member is rotated with respect to the housing so as to rotate the locking member and the elongated member with respect to the housing.

6. The treatment tool of claim 1,
wherein the locking member is released from fitting engagement with the housing for rotation against the biasing forces of the biasing member depending on relative rotation between the rotary member and the housing, to unlock the elongated member from the housing for rotation, and the locking member is fitted into the housing to lock the elongated member against rotation with respect to the housing under the biasing forces of the biasing member upon stopping of relative rotation between the rotary member and the housing.

7. The treatment tool of claim 1, wherein the end effector is disposed in a position off the rotational axis.

8. The treatment tool of claim 1, wherein the end effector is bendable with respect to the elongated member.

* * * * *